United States Patent [19]

Brown et al.

[11] Patent Number: 4,587,355

[45] Date of Patent: May 6, 1986

[54] OXIDATION WITH A SOLID CATALYST

[75] Inventors: Albert P. Brown, Downers Grove; John G. Hundley, St. Charles, both of Ill.

[73] Assignee: Amoco Corporation, Chicago, Ill.

[21] Appl. No.: 643,153

[22] Filed: Aug. 22, 1984

[51] Int. Cl.$^4$ ............................................ C07C 51/265
[52] U.S. Cl. ...................................................... 562/414
[58] Field of Search ................................ 562/414, 416

[56] References Cited

U.S. PATENT DOCUMENTS 3,708,531  1/1973  Croce et al. ........................ 562/416
4,490,297  12/1984 Feld et al. ...................... 562/414 X
4,490,298  12/1984 Feld .............................. 562/414 X Primary Examiner—Natalie Trousof
Assistant Examiner—Patricia M. Scott
Attorney, Agent, or Firm—James R. Henes; William T. McClain; William H. Magidson

[57] ABSTRACT

A method is disclosed for the liquid phase oxidation of an alkyl aromatic in the presence of an oxidation catalyst comprising cobalt, manganese and bromine components wherein at least a portion of the cobalt and manganese components are solid cobalt and manganese oxalates.

8 Claims, No Drawings

OXIDATION WITH A SOLID CATALYST

BACKGROUND OF THE INVENTION

1. Field of the Invention

This invention relates generally to the liquid phase oxidation of an alkyl aromatic in a solvent with an oxygen-containing gas under an elevated temperature and pressure and in the presence of an oxidation catalyst comprising cobalt, manganese and bromine components, and more particularly concerns a method for effecting this oxidation process using solid cobalt and manganese oxalates as catalyst components.

2. Description of the Prior Art

The liquid phase oxidations of an alkyl aromatic in an acetic acid medium with an oxygen-containing gas are frequently performed in the presence of an oxidation catalyst comprising cobalt, manganese and bromine components. The failure to recover and re-use the cobalt and manganese components of the catalyst system after the liquid phase oxidation represents a significant economic loss and raises a potential environmental problem of disposal. Even when the mother liquor resulting after separation of the aromatic carboxylic acid product and containing dissolved catalyst is recycled to the aforesaid liquid phase oxidation, since undesirable organic by-products accumulate in the mother liquor, generally a portion of the separated mother liquor is not recycled but is discharged as residue. The cobalt and manganese components of this unrecycled portion of the mother liquor are therefore also discharged. Because the recovery of the cobalt and manganese components of the catalyst after completion of the oxidation represents an important factor for the economic operation of such a process, recovery of the cobalt and/or manganese components of the catalyst system by their precipitation as solid oxalates from the organic media has been proposed. For example, Japanese Kokai Pat. No. 51/97592, published British Patent Application No. 2,114,130 and U.S. Pat. Nos. 3,840,469 and 4,246,185 disclose such methods. However, processes to solubilize the cobalt and manganese oxalates and then to use the soluble forms of cobalt and manganese as catalyst components in the aforesaid liquid phase oxidations tend to be complex and costly. Thus, if they could be used directly as catalyst components in the aforesaid liquid phase oxidations of alkyl aromatics, the resulting solid cobalt and manganese oxalates represent a convenient, immediately available, economical and highly desirable source of catalyst material. However, heretofore the direct use of solid cobalt oxalate and/or manganese oxalate from any source—and in particular as recycled from an aforesaid oxalate precipitation technique for recovery of the cobalt and manganese catalyst components—as catalyst components in the aforesaid liquid phase oxidations of alkyl aromatics has not been proposed. For example, U.S. Pat. No. 3,840,469 teaches that the precipitated cobalt oxalate be redissolved as cobalt acetate in an acetic acid solution which could then be used in the liquid phase oxidation.

OBJECTS OF THE INVENTION

It is therefore a general object of the present invention to provide an improved method for the liquid phase oxidation of an alkyl aromatic with an oxygen-containing gas in a solvent and in the presence of an oxidation catalyst comprising cobalt, manganese and bromine components, which meets the aforementioned goals and solves the aforementioned problems.

More particularly, it is an object of the present invention to provide an improved method for effecting the aforesaid oxidation process in the presence of solid cobalt and manganese oxalates as catalyst components.

It is a related object of the present invention to provide an improved oxidation process by recovering the cobalt and manganese components of the catalyst after completion of the oxidation by their precipitation as solid oxalates and then recycling the solid cobalt and manganese oxalates for direct use as catalyst components in the aforesaid liquid phase oxidation.

Other objects and advantages of the invention will become apparent upon reading the following detailed description and appended claims.

SUMMARY OF THE INVENTION

These objects are achieved by an improved method for producing an aromatic carboxylic acid by the liquid phase oxidation of an alkyl aromatic with an oxygen-containing gas in a solvent at an elevated temperature and pressure and in the presence of an oxidation catalyst comprising cobalt, manganese and bromine components, wherein at least a portion of the cobalt and manganese catalyst components initially contacted with the alkyl aromatic and oxygen-containing gas is in the form of solid cobalt and manganese oxalates.

DETAILED DESCRIPTION OF THE PREFERRED EMBODIMENTS

Suitable alkyl aromatics for use in the method of this invention include toluene, o-, m- and p-xylene, and the trimethylbenzenes. The respective aromatic carboxylic acid products formed are benzoic acid, orthophthalic acid, isophthalic acid, terephthalic acid and the aromatic tricarboxylic acids. In a preferred embodiment of the method of this invention, m-xylene is oxidized to isophthalic acid.

Suitable solvents for use in the method of this invention include any $C_2$–$C_6$ fatty acids such as acetic acid, propionic acid, n-butyric acid, isobutyric acid, n-valeric acid, trimethylacetic acid and caproic acid and water and mixtures thereof. Preferably, the solvent is a mixture of acetic acid and water, which more preferably contains from 1 to 20 weight percent of water, as introduced into the oxidation reactor. The weight ratio of the solvent-to-alkyl aromatic introduced into the reactor in the liquid phase oxidation of this invention is in the range of from about 19:1, preferably from about 6:1, to about 3:1, preferably to about 4:1.

The source of molecular oxygen for the oxidation of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 2 to 8 volume percent oxygen (measured on a solvent-free basis). For example, when each alkyl substituent on the aromatic ring of the alkyl aromatic is a methyl group, a feed rate of the oxygen-containing gas sufficient to provide oxygen in the amount of from 1.6 to 2.8 moles per methyl group will provide such 2 to 8 volume percent of oxygen (measured on a solvent-free basis) in the gas-vapor mixture in the condenser.

The catalyst employed in the method of this invention comprises cobalt, manganese and bromine components. The weight ratio of cobalt (calculated as elemental cobalt) in the cobalt component of the catalyst-to-the alkyl aromatic in the liquid phase oxidation of the method of this invention is in the range of from about 0.5 to about 10 milligram atoms (mga) per gram mole of the alkyl aromatic. The weight ratio of manganese (calculated as elemental manganese) in the manganese component of the catalyst-to-cobalt (calculated as elemental cobalt) in the cobalt component of the catalyst in the liquid phase oxidation of the method of this invention is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid phase oxidation of the method of this invention is in the range of from about 0.2 to about 1.5 mga per mga of total cobalt and manganese.

At least a portion of the cobalt and manganese components introduced into the liquid phase oxidation is in the form of solid cobalt and manganese oxalates. Up to 100 weight percent of the total amount of each of the cobalt and manganese components of the catalyst employed in the liquid phase oxidation of this invention is initially contacted with the alkyl aromatic feed and oxygen in the form of solid cobalt oxalate ($Co(C_2O_4)\cdot O-2H_2O$) and solid manganese oxalate ($Mn(C_2O_4)\cdot O-3H_2O$). As introduced into the liquid phase oxidation of the method of this invention, the solid cobalt and manganese oxalates must be of a particle size suitable for slurrying in the reaction mixture in the oxidation reactor. Suitably, the cobalt and manganese oxalates are from 5 to 200 microns in their largest dimension.

The remainder, if any, of the total amount of the cobalt and manganese components of the catalyst employed in the liquid phase oxidation of this invention is introduced into the oxidation reactor as forms of cobalt and manganese that are soluble in the solvent.

In the event that soluble forms of the cobalt and manganese components are introduced into the liquid phase oxidation of this invention, each of the cobalt and manganese components can be provided in any of its known ionic or combined forms that are soluble in the solvent. For example, when the solvent is an acetic acid medium, cobalt and/or manganese carbonate, acetate tetrahydrate, and/or bromide can be employed. The 0.2 to 1.5:1.0 elemental bromine-to-total cobalt and manganese milligram atom ratio is provided by a source of bromine. Such bromine sources include elemental bromine ($Br_2$), or ionic bromide (for example, HBr, Na or KBr, $NH_3Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-dibromide, etc.). The total bromine in molecular bromine and ionic bromide is used to determine satisfaction of the elemental bromine to total cobalt and manganese milligram atom ratio of 0.2–1.5:1.0. The bromide ion released from the organic bromides at the oxidation operating conditions can be readily determined by known analytical means. Tetrabromoethane, for example, at operating temperatures such as 170° to 225° C. has been found to yield about 3 effective gram atoms of bromine per gram mole.

In operation, the minimum pressure at which the reactor is maintained is that pressure which will maintain a substantial liquid phase of the alkyl aromatic and at least 70 percent of the solvent. The alkyl aromatic and solvent not in the liquid phase because of vaporization is removed from the reactor as a vapor-gas mixture, condensed and then returned to the reactor in the recycle solvent. When the solvent is an acetic acid-water mixture, suitable reaction gauge pressures are in the range off from about 0 $kg/cm^2$ to about 35 $kg/cm^2$, and typically are in the range of from about 10 $kg/cm^2$ to about 30 $kg/cm^2$.

The temperature range within the reactor is generally from about 120° C., preferably from about 150° C., to about 240° C., preferably to about 230° C. Within these broad ranges, various narrower ranges are generally preferred depending on the particular alkyl aromatic being oxidized. For example, when the alkyl aromatic is m-xylene, the preferred temperature within the reactor is in the range of from about 150° C. to about 225° C.

In a preferred embodiment of the method of this invention, the solid cobalt and manganese oxalates introduced into the liquid phase oxidation are obtained by introducing either solid oxalic acid or a solid metal oxalate or an aqueous solution of either thereof into at least a portion of the product stream withdrawn from the oxidation reactor to precipitate cobalt and manganese ions therein as cobalt and manganese oxalates and then separating the cobalt and manganese oxalate precipitates and recycling them to the liquid phase oxidation. Metal oxalates suitable for introduction into the product stream include sodium oxalate, potassium oxalate, lithium oxalate, cesium oxalate and ammonium oxalate.

In this preferred embodiment, generally at least a major portion of the aromatic carboxylic acid product is separated from the product stream before the oxalic acid or metal oxalate is introduced into the product stream. If the aromatic carboxylic acid product is soluble in the product stream withdrawn from the reactor—for example, isophthalic acid in an acetic acid-water solvent—this can be done by cooling the product stream to a temperature where the aromatic carboxylic acid crystallizes from the product stream. The crystallized aromatic carboxylic acid product is then separated from the product stream by any convenient method—for example, by centrifugation or filtration—and thereafter oxalic acid or the metal oxalate is introduced into the product stream. For example, for isophthalic acid in an acetic acid solvent, the product stream is cooled to a temperature in the range of from about 90° C. to about 120° C. to crystallize the isophthalic acid which is then removed before oxalic acid or the metal oxalate is added. Most preferably, after the crystallized isophthalic acid has been crystallized at a temperature in the range of from abut 90° C. to about 120° C. and removed, the product stream is further cooled to a temperature in the range of from about 40° C. to about 75° C. before, while or after the oxalic acid or metal oxalate is added, to precipitate both cobalt and manganese oxalates and additional isophthalic acid dissolved or suspended in the product stream. This additional amount of isophthalic acid, together with the solid cobalt and manganese oxalates, is then recycled to the liquid phase oxidation and is finally recovered from the product stream.

As the liquid phase oxidation of an alkyl aromatic to an aromatic carboxylic acid is commonly practiced commercially, after recovery of the aromatic carboxylic acid product from the product stream, the product stream, including the cobalt and manganese ions dissolved therein, is recycled to the oxidation reactor. However, since undesirable organic by-products accumulate in the reaction mixture, generally a portion of the product stream is not recycled but is discharged as residue in order to reduce the buildup of such by-products. In this instance, the oxalic acid or metal oxalate is introduced into that portion of the product stream which is not to be recycled in order to recover the cobalt and manganese components therefrom before it is discharged.

Stoichiometrically, one mole of oxalic acid and/or the oxalate ion can react with one gram atom of each of the cobalt or manganese ion to form the corresponding hydrated salt. However, since the extent of this reaction is influenced by the concentration of the reactants, the pH and temperature of the medium, the presence of oxygen and other factors, the number of moles of oxalic acid and/or oxalate ion to be added per gram atom of total cobalt and manganese content of the stream needed to attain the desired recovery of cobalt and manganese is a function of the overall composition, pH and temperature of the stream and must be determined on a case-by-case basis.

The present invention will be more clearly understood from the following specific examples.

EXAMPLES 1-22

Recovery of cobalt and manganese dissolved in product streams resulting from the liquid phase oxidation of alkyl aromatics is demonstrated in Examples 1-22 using mother liquor samples—that is, samples of product streams from the liquid phase oxidation of an alkyl aromatic to an aromatic carboxylic acid from which the aromatic carboxylic acid had already been substantially removed by crystallization—from a commercial unit for the production of isophthalic acid from m-xylene. The compositions of the mother liquor samples employed are indicated in Table 1.

Mother liquors A and B were employed in Examples 1-11 and in Examples 12-22, respectively. In each of Examples 1-22, a volume of the mother liquor employed in that example, which had been heated to dissolve all suspended solids, was cooled, either relatively slowly or rapidly under vacuum, to 165° F., and then reagent grade oxalic acid dihydrate was added in the form of its solution in approximately 25 grams of water, and the mixture was held for 5 hours at 165° F. The precipitate which formed was recovered by vacuum filtration and the resulting unwashed filter cakes were allowed to dry at ambient conditions. For each of Examples 1-22, the weight of mother liquor, the number of moles of oxalic acid per gram atom of total cobalt and manganese in the weight of mother liquor (reported as Oxalic Acid Ratio), the weight and cobalt and manganese contents of the resulting filtrate, the recovery of cobalt and manganese from the mother liquor (calculated as the difference between the cobalt and manganese contents of the mother liquor and the cobalt and manganese contents, respectively, of the filtrate) and the weight of the resulting filter cake are reported in Table 2.

EXAMPLES 23-31

The direct use of solid cobalt and manganese oxalates as catalyst components in the liquid phase oxidation of m-xylene to isophthalic acid in an acetic acid medium is demonstrated in Examples 24, 26 and 29-31. In each of Examples 24, 26, 29 and 30, approximately 70 weight percent of each of the cobalt and manganese catalyst components (calculated as the elemental metals) was in the form of the solid metal oxalate. In Example 31, 100 weight percent of each of the cobalt and manganese catalyst components was in the form of the solid metal oxalate and, in addition, excess free oxalic acid was added to afford 1.4 moles of oxalic acid and/or oxalate per gram atom of cobalt and manganese combined. Comparative Examples 23, 25, 27 and 28 demonstrate the use of dissolved cobalt and manganese acetate tetrahydrate as catalyst components in the liquid phase oxidation of m-xylene to isophthalic acid under substantially the same conditions as those employed in Examples 24, 26 and 29-31, respectively. Examples 23 and 24 were performed on a batch basis, Examples 25 and 26 were performed semi-continuously, and Examples 27-31 were performed continuously.

TABLE 1

| COMPOSITION OF MOTHER LIQUORS | | |
|---|---|---|
| Mother Liquor | A | B |
| Organic, wt. % | | |
| Benzoic Acid | NA[1] | 0.59 |
| m-Toluic Acid | NA | 0.062 |
| m-Tolualdehyde | NA | NA |
| Isophthalic Acid | NA | 1.71 |
| 3-Carboxybenzaldehyde | NA | 0.11 |
| Hemimellitic Acid | NA | 0.05 |
| Trimellitic Acid | NA | 0.27 |
| Trimesic Acid | NA | — |
| Terephthalic Acid | NA | 0.21 |
| High Mol. Wt. Components | NA | 0.851 |
| Inorganic, ppm | | |
| Cobalt | 77 | 156 |
| Manganese | 700 | 485 |
| Mn: Co Weight Ratio | 9:1 | 3:1 |
| Iron | 1 | 3 |
| Nickel | <0.4 | <0.4 |
| Sodium | 35 | 28 |
| Chromium | <0.4 | <0.4 |
| $H_2O$, Wt. % | 10.5 | 11.1 |

Footnote
[1]Not Analyzed

TABLE 2

| Example | Wt. Mother Liquor, g | Oxalic Acid Ratio | Filtrate Wt, g | Filtrate Co, ppm | Filtrate Mn, ppm | Recovery, Wt. % Co | Recovery, Wt. % Mn | Cake, g |
|---|---|---|---|---|---|---|---|---|
| 1 | 763.3 | 0.1 | 767.2 | 38 | 630 | 51 | 10 | 5.02 |
| 2 | 761.9 | 0.25 | 762.4 | 9 | 545 | 88 | 22 | 5.56 |
| 3 | 707.7 | 0.5 | 715.1 | 2 | 360 | 97 | 48 | 3.31 |
| 4 | 782.0 | 0.75 | 780.9 | <0.4 | 178 | >99.5 | 75 | 5.63 |
| 5 | 703.1 | 0.9 | 709.0 | <0.4 | 86 | >99.5 | 88 | 5.74 |
| 6 | 687.3 | 1.00 | 685.9 | <0.4 | 56 | >99.5 | 92 | 6.03 |
| 7 | 773.4 | 1.1 | 771.4 | <0.4 | 41 | >99.5 | 94 | 6.81 |
| 8 | 697.4 | 1.25 | 693.3 | <0.4 | 28 | >99.5 | 96 | 5.94 |
| 9 | 685.3 | 1.5 | 686.8 | <0.4 | 23 | >99.5 | 97 | 5.32 |
| 10 | 761.1 | 1.75 | 722.6 | <0.4 | 13 | >99.5 | 98 | 4.24 |

TABLE 2-continued

| Example | Wt. Mother Liquor, g | Oxalic Acid Ratio | Filtrate Wt, g | Co, ppm | Mn, ppm | Recovery, Wt. % Co | Mn | Cake, g |
|---|---|---|---|---|---|---|---|---|
| 11 | 758.5 | 2.0 | 767.7 | <0.4 | 14 | >99.5 | 98 | 3.33 |
| 12 | 807.3 | 0.1 | 800.8 | 109 | 460 | 31 | 6 | 6.02 |
| 13 | 838.5 | 0.25 | 837.7 | 83 | 384 | 47 | 21 | 6.49 |
| 14 | 823.9 | 0.5 | 821.3 | 12 | 288 | 92 | 41 | 7.15 |
| 15 | 831.0 | 0.75 | 824.5 | 0.7 | 152 | >99.5 | 69 | 6.66 |
| 16 | 672.5 | 0.9 | 678.9 | 0.4 | 98 | >99.5 | 80 | 4.94 |
| 17 | 738.6 | 1.0 | 734.2 | 0.4 | 78 | >99.5 | 84 | 6.92 |
| 18 | 846.1 | 1.1 | 837.9 | 0.4 | 56 | >99.5 | 89 | 8.18 |
| 19 | 676.7 | 1.25 | 679.2 | 0.4 | 41 | >99.5 | 92 | 6.15 |
| 20 | 824.2 | 1.5 | 816.9 | 0.4 | 39 | >99.5 | 92 | 7.32 |
| 21 | 813.6 | 1.75 | 806.7 | 0.4 | 26 | >99.5 | 95 | 7.05 |
| 22 | 801.8 | 2.0 | 798.5 | 0.4 | 27 | >99.5 | 94 | 4.15 |

Examples 23–26 were performed using a one-liter titanium pressure vessel as the oxidation reactor, equipped with an overhead condenser for condensation of the solvent and m-xylene which vaporized in the reactor and also for return of the condensed material to the reaction mixture in the reactor. A stainless steel vessel was employed as the receiver for product withdrawn from the reactor. In the batch oxidations of Examples 23 and 24, the reactor was initially charged with the full amounts of m-xylene, solvent (an acetic acid-water mixture) and catalyst (cobalt, manganese and bromine components) employed, and oxygen was continuously supplied to the reactor at a rate sufficient to maintain the reactor at a pressure of 400 psig and was continued until the oxygen content of the overhead vapor (on a solvent-free basis) reached 16–18 volume percent, at which point the oxidation was complete. The reaction mixture was stirred throughout the oxidation at 800 rpm. The contents of the reactor were first heated to about 170° C. where the reaction was initiated by the introduction of air, whereupon the temperature of the reactor contents quickly rose to the desired temperature for the remainder of the reaction time. In the semi-continuous oxidations of Examples 25 and 26, the same procedure and conditions were employed as in Examples 23 and 24 except that all of the solvent and catalyst employed but only 10 grams of m-xylene were initially charged to the reactor, and, once the reaction was initiated at about 170° C., the remainder of the total amount of m-xylene employed was continuously pumped into the reactor at a rate of 2 milliliters per minute. The materials, amounts thereof, and conditions employed in, and the results of, Examples 23–26 are reported in Table 3.

In the continuous oxidation of Examples 27–31, the reaction components, including m-xylene, the solvent (a mixture of acetic acid and water) and the catalyst, were adding continuously as a single mixture during the course of the reaction. A small initial charge of the above mixture was first batch oxidized to initiate the reaction, after which the continuous oxidation of the reaction components was begun.

The continuous reactions were conducted in a stirred 6.5 liter titanium pressure vessel. This vessel was equipped with an overhead condenser for condensation of the solvent and m-xylene which vaporized in the reactor and also for return of the condensed material to the reaction mixture in the reactor. During a period when the reaction was approaching steady-state conditions, product was intermittently withdrawn, to maintain a desired liquid level within the reactor, and then transferred to one of two adjoining titanium receiving vessels. Once steady-state conditions were achieved, product was similarly colllected in the second receiving vessel for analysis. The materials, amounts thereof and conditions employed in Examples 27–31 are reported in Table 4, and the results of Examples 27–31, including the results of analyses of the isophthalic acid produced therein, are reported in Table 5.

TABLE 3

| Example No. | 23 | 24 | 25 | 26 |
|---|---|---|---|---|
| Materials, g | | | | |
| m-xylene | 140 | 140 | 140 | 140 |
| solvent | | | | |
| acetic acid | 500 | 500 | 500 | 500 |
| water | 10 | 10 | 10 | 10 |
| catalyst composition | | | | |
| soluble | | | | |
| cobalt acetate tetrahydrate | 0.30 | 0.10 | 0.28 | 0.10 |
| manganese acetate tetrahydrate | 0.81 | 0.25 | 0.87 | 0.25 |
| 48% HBr | 0.75 | 0.75 | 0.75 | 0.75 |
| insoluble | | | | |
| cobalt oxalate dihydrate | — | 0.14 | — | 0.14 |
| manganese oxalate dihydrate | — | 0.46 | — | 0.46 |
| Mn:Co:Br gram atom ratio | 3:1:4 | 3:1:4 | 3:1:4 | 3:1:4 |
| Conditions | | | | |
| temperature, °C. | 226 | 228 | 230 | 226 |
| run time, min. | 50 | 70 | 75 | 75 |
| O$_2$ in vent gas, vol % | 2–8 | 2–8 | 2–8 | 2–8 |
| Results | | | | |
| Yields, mole | | | | |
| CO | 0.27 | 0.38 | 0.49 | 0.42 |
| CO$_2$ | 0.66 | 1.16 | 1.33 | 1.29 |
| CO$_x$, mole % of m-xylene[1] | 8.8 | 14.6 | 17.0 | 18.2 |
| O$_2$ uptake, mole % of m-xylene | 100 | 117 | 100 | 118 |

Footnote
[1] Assumes all CO$_x$ formed from m-xylene

TABLE 4

| Example No. | 27 | 28 | 29 | 30 | 31 |
|---|---|---|---|---|---|
| Materials, wt. % | | | | | |
| m-xylene | 20.5 | 20.5 | 20.5 | 20.5 | 20.5 |
| solvent | | | | | |
| acetic acid | Balance | Balance | Balance | Balance | Balance |

TABLE 4-continued

| Example No. | 27 | 28 | 29 | 30 | 31 |
|---|---|---|---|---|---|
| water | 7.0 | 7.0 | 7.0 | 7.0 | 7.0 |
| catalyst composition | | | | | |
| soluble | | | | | |
| cobalt acetate tetrahydrate | 0.063 | 0.063 | 0.020 | 0.020 | 0 |
| manganese acetate tetrahydrate | 0.201 | 0.201 | 0.061 | 0.061 | 0 |
| 48% HBr | 0.063 | 0.063 | 0.063 | 0.063 | 0.063 |
| insoluble | | | | | |
| cobalt oxalate dihydrate | 0 | 0 | 0.033 | 0.033 | 0.047 |
| manganese oxalate dihydrate | 0 | 0 | 0.103 | 0.103 | 0.147 |
| Mn:Co:Br gram atom ratio | 3.2:1:1.5 | 3.2:1:1.5 | | 3.2:1:1.5 | 3.2:1:1.5 |
| Conditions | | | | | |
| temperature, °C. | 222 | 222 | 222 | 222 | 222 |
| residence time, min. | 45 | 45 | 45 | 45 | 45 |
| $O_2$ in vent gas, vol. % | 2–3 | 2–3 | 2–3 | 2–3 | 2–3 |

TABLE 5

| Example No. | 27 | 28 | 29 | 30 | 31 |
|---|---|---|---|---|---|
| yields, mole % | | | | | |
| isophthalic acid | 94.51 | 84.30 | 88.33 | 91.66 | 82.69 |
| carbon oxides | 3.91 | 3.85 | 3.56 | 3.62 | 3.73 |
| m-xylene | 0 | 0 | 0 | 0 | 0 |
| m-tolualdehyde | 0.250 | 0.231 | 0.258 | 0.293 | 0.252 |
| m-toluic acid | 1.989 | 1.528 | 2.001 | 2.194 | 1.578 |
| 3-carboxybenzalhyde | 0.882 | 0.555 | 0.784 | 0.897 | 0.556 |
| benzoic acid | 1.035 | 1.021 | 1.034 | 0.959 | 0.986 |
| hemimellitic acid | 0.109 | 0.144 | 0.094 | 0.095 | 0.141 |
| trimellitic acid | 0.344 | 0.306 | 0.277 | 0.262 | 0.311 |
| trimesic acid | 0.089 | 0.044 | 0.068 | 0.031 | 0.043 |
| terephthalic acid | 0.239 | 0.191 | 0.233 | 0.507 | 0.187 |
| high molecular weight acids[1] | 1.025 | 0.903 | 0.848 | 0.877 | 0.847 |
| carbon oxides[2] | 0.626 | 0.617 | 0.569 | 0.579 | 0.597 |
| acetic acid loss[3] | 0.0886 | 0.0873 | 0.0805 | 0.0819 | 0.0844 |
| $O_2$ uptake[2] | 3.64 | 3.41 | 3.35 | 3.40 | 3.41 |
| Isophthalic acid quality | | | | | |
| cobalt, ppm | <2 | <2 | <2 | <2 | <2 |
| manganese, ppm | <2 | 2 | <2 | <2 | 2 |
| bromine, ppm | 26 | 29 | 29 | 28 | 28 |
| $OD_{340}$ | 1.97 | NA[4] | 1.84 | 1.76 | 1.89 |

Footnotes
[1] compounds with 2 or more aromatic rings
[2] moles per mole of m-xylene in the feed
[3] weight per weight of m-xylene, based on carbon oxide formation and assuming 50 mole % of carbon oxides form from acetic acid
[4] not analyzed.

Examples 1–22 illustrate the efficiency of oxalic acid in recovering cobalt and manganese from an acetic acid mother liquor stream. In Examples 1–22, a broad range of Oxalic Acid Ratios (eqivalent to from 10 to 200 weight percent of the stoichiometric amount of oxalic acid based on the total amount of cobalt and manganese) was employed. The results of Examples 1–22 illustrate that essentially quantitative recovery of cobalt can be achieved at relatively low Oxalic Acid Ratios. For example, when a ratio of 0.75 mole of oxalic acid per gram atom of cobalt and manganese combined, 99.5 weight percent of the cobalt was recovered from the mother liquor; at the same time, 70–75 weight percent of the manganese was also recovered. Furthermore, the precipitation of the cobalt and manganese oxalates occurred rapidly, with 96 weight percent and 93 weight percent of the amounts of cobalt oxalate, and manganese oxalate, respectively, actually recovered being recovered within a half hour. Moreover, although aqueous solutions of oxalic acid were employed, other work proved that the same high recoveries of cobalt and manganese in Examples 1–22 were obtained with the addition of solid oxalic acid to effect precipitation as with the addition of an aqueous solution of oxalic acid.

The results of Examples 27–31 illustrate that there is no apparent adverse effect on the quality of the isophthalic acid product from the use of solid cobalt and manganese oxalates relative to the isophthalic acid product from the use of soluble cobalt and manganese acetates. These results indicate that the use of solid cobalt and manganese oxalate catalyst components does not cause an increase in the concentration of cobalt, manganese or undesirable higher boiling, organic by-products in the isophthalic acid products. For example, the cobalt and manganese concentrations of the isophthalic acid cakes produced in Examples 29–31 are at the same levels as the cobalt and manganese concentrations of the isophthalic acid cakes produced in Examples 27–28. Furthermore, the optical densities of the isophthalic acid produced in Examples 29–31 are essentially the same as the optical densities of the isophthalic acid produced in Examples 27–28. The optical density of isophthalic acid (5 grams of isophthalic acid in 30 milliliters of 3.0N ammonium hydroxide) at 340 nanometers is used to evaluate product quality.

In addition, Examples 27–31 illustrate that the use of solid cobalt and manganese oxalate catalyst components affords essentially the same relative product distribution as does the use of only soluble cobalt and manganese acetate catalyst components. Thus, the use of the solid oxalates has no effect on the course of the oxidation reaction with regard to product yields. Furthermore, no operating problems or reaction instabilities were observed in any of the runs involving the use of solid cobalt and manganese oxalate catalyst components. Moreover, although the production of carbon oxides—which indicates burning of the m-xylene and/or acetic acid—was higher in the batch and semi-continuous runs involving solid cobalt and manganese oxalate catalyst components relative to the runs involving soluble cobalt and manganese acetates, there was no such increase in the continuous runs, which more closely approximated the conditions and operation of a commercial unit. The excess of oxalic acid and/or oxalate in Example 31 had no observable adverse effect on the oxidation reaction or the resulting product.

Having described the invention, what is claimed is:

1. A method for producing an aromatic carboxylic acid by the liquid phase oxidation of an alkyl aromatic with an oxygen-containing gas in a solvent at an elevated temperature and pressure and in the presence of an oxidation catalyst comprising cobalt, manganese and bromine components, wherein at least a portion of the cobalt and manganese catalyst components initially contacted with the alkyl aromatic and oxygen-containing gas is in the form of solid cobalt and manganese oxalates, wherein (1) the resulting reaction mixture comprised the aromatic carboxylic acid product and cobalt and manganese cations dissolved in the solvent, (2) at least a major portion of the aromatic carboxylic acid product is separated from the solvent, (3) oxalic acid or an oxalate salt is introduced into at least a portion of the solvent to precipitate cobalt and manganese oxalates, and (4) the precipitated cobalt and manganese oxalates are separated from the solvent and recycled to the liquid phase oxidation.

2. The method of claim 1 wherein the solvent is an acetic acid medium.

3. The method of claim 1 wherein the temperature is in the range of from about 120° C. to about 240° C.

4. The method of claim 1 wherein the oxygen-containing gas is air.

5. The method of claim 1 wherein m-xylene is the alkyl aromatic and isophthalic acid is the aromatic carboxylic acid.

6. The method of claim 5 wherein the temperature is in the range of from about 150° C. to about 225° C.

7. The method of claim 1 wherein the cobalt component, calculated as elemental cobalt, is present at a level of 0.5 to 10 milligram atoms per gram mole of the alkyl aromatic, the manganese component, calculated as elemental manganese, is present at a level of 0.2 to 10 milligram atoms per milligram atom of cobalt, and the bromine component, calculated as elemental bromine, is present at a level of 0.2 to 1.5 gram atoms per gram atom of total cobalt and manganese.

8. The method of claim 1 wherein the alkyl aromatic is m-xylene and the aromatic carboxylic acid product is isophthalic acid and wherein in step (2) the solvent is cooled to a temperature in the range of from about 90° C. to about 120° C. to precipitate a major portion of the isophthalic acid which is then separated from the solvent, and a major portion of the resulting solvent is recycled to the liquid phase oxidation, and in step (3) the resulting solvent is cooled to a temperature in the range of from about 40° C. to about 75° C. to precipitate additional isophthalic acid, and in step (4) the precipitated isophthalic acid and cobalt and manganese oxalates are separated from the solvent and recycled to the liquid phase oxidation.

* * * * *

UNITED STATES PATENT OFFICE
CERTIFICATE OF CORRECTION

Patent No. 4,587,355          Dated May 6, 1986

Inventor(s)   Albert P. Brown & John G. Hundley

It is certified that error appears in the above-identified patent and that said Letters Patent are hereby corrected as shown below:

Column 3, line 27, ".O-2$H_2$O" should be --•O-2$H_2$O--.

Column 3, line 28, ".O-3$H_2$O" should be --•O-3$H_2$O--.

Signed and Sealed this

Twenty-third Day of September 1986

[SEAL]

Attest:

DONALD J. QUIGG

Attesting Officer   Commissioner of Patents and Trademarks